(12) United States Patent
Chiarello et al.

(10) Patent No.: US 6,670,184 B2
(45) Date of Patent: Dec. 30, 2003

(54) METHOD FOR PRODUCING A LIPID EMULSION FOR USE IN INSECT CELL CULTURE

(75) Inventors: Ronald H. Chiarello, Castro Valley, CA (US); Sarah Himmerich, San Francisco, CA (US)

(73) Assignee: BASF AG, Ludwigshafen (DE)

( * ) Notice: Subject to any disclaimer, the term of this patent is extended or adjusted under 35 U.S.C. 154(b) by 0 days.

(21) Appl. No.: 09/887,149

(22) Filed: Jun. 21, 2001

(65) Prior Publication Data

US 2002/0119567 A1 Aug. 29, 2002

Related U.S. Application Data

(60) Provisional application No. 60/213,665, filed on Jun. 23, 2000.

(51) Int. Cl.[7] .............................. C12N 1/04; C12N 5/00; C12N 5/02; C12N 5/04; C12N 5/10
(52) U.S. Cl. ........................ 435/404; 435/260; 435/348
(58) Field of Search ................................. 210/634, 600; 435/4, 458, 243, 260, 266, FOR 179, 348, 271, 404; 424/1.21, 9.321, 9.51, 417, 420, 450, 94.3, 812

(56) References Cited

U.S. PATENT DOCUMENTS 5,024,947 A  6/1991  Inlow et al. ................ 435/240
5,372,943 A  12/1994  Inlow et al. ................ 435/240

OTHER PUBLICATIONS

Vaughn et al. "Differential Requirements of Two Insect Cell Lines for Growth in Serum–Free Medium" In Vitro Cell. Dev. Biol. vol. 33 (1997) pp. 479–482.

Donaldson et al. "Low–Cost Serum–Free Medium for the BTI–Tn5B1–4 Insect Cell Line" Biotechnology Prog. vol. 14 (1998) pp. 573–579.

Hink "A Serum–Free Medium for the Culture of Insect Cells and Production of Recombinant Proteins" In Vito Cell Dev. Biol. vol. 27A (1991) pp. 397–401.

*Primary Examiner*—David M. Naff
*Assistant Examiner*—Deborah K. Ware
(74) *Attorney, Agent, or Firm*—Licata & Tyrrell P.C.

(57) ABSTRACT

A serum-free insect cell culture medium is provided which provides improvements in the maximum insect cell density and replication of insect viruses within these cells, at a significantly lower cost than commercially-available media. A method is provided for preparing a lipid emulsion for use in insect culture media for large scale culture, and which produces a more stable emulsion with a longer shelf life. The method is preferably carried out by combining in an organic solvent a surfactant and a mixture of lipids to make a lipid phase, heating the lipid phase to a temperature of 40 to 70 degrees Celsius to form an anhydrous lipid phase and adding an aqueous phase thereto to provide a stable lipid microemulsion.

5 Claims, 1 Drawing Sheet

METHOD FOR PRODUCING A LIPID EMULSION FOR USE IN INSECT CELL CULTURE

This application claims the benefit of provisional Application No. 60/213,665, filed Jun. 23, 2000.

FIELD OF THE INVENTION

The present invention relates to fermentation and cell culture, and more particularly, to cell culture media and concentrated lipid emulsions for use therein.

BACKGROUND OF THE INVENTION

Many recent developments in biotechnology, such as the industrial production of viral insecticides, recombinant products and the like via insect cell lines, require in vitro cell culture on a large scale, which in turn demands considerable amounts of cell culture media. Unfortunately, the serum and serum albumin found in conventional cell culture media is problematic, and can be cost-prohibitive for large-scale tank fermentation. The serum-free alternatives described thus far in the prior art are also costly in large volumes.

The major problem with most commercially-available media is the need to supplement the media with a large serum component (typically 5–20%), which creates a significant limiting factor due to the high price and limited availability of the serum. Moreover, the use of animal serum and/or serum albumin in the media is also problematic from a production standpoint, since the presence of unidentified proteins in the sera can complicate downstream efforts at product purification and contaminating animal viruses can pose serious safety issues. Similarly, the unidentified proteins found in these materials introduce an unwanted variable into smaller-scale experimental efforts as well. Further, the quality of the sera itself can vary from lot to lot, introducing a contamination risk which must be investigated and resolved by the scientist or production engineer with each change in sera.

Another related problem with the use of serum and/or serum albumin in cell culture media involves their conventional role as the carrier for the lipid component, an essential requirement for most cell culture work. Since the direct addition of lipids to the media is impractical due to their low solubility, they are typically introduced along with the serum component in the form of water soluble lipoproteins. Alternatively, the lipids can be bound to the albumin component and then added to media. Given the difficulties noted above with respect to the use of these materials, however, it would be advantageous to provide a suitable lipid emulsion which does not require either serum or albumin. Iscove, "Culture of Lymphocytes and Hematopoietic Cells in Serum-Free Medium," in Barnes et al., *Methods for Serum-Free Culture of Neuronal and Lymphoid Cells*, pp. 169–85 (1984). Although microemulsions have been described in the art to supply the necessary lipids for conventional insect serum-free media, Maoiella et al, *Bio/Technology*, 6:1406 (1988), these prior art emulsions have proven unsatisfactory for a variety of reasons, including high manufacturing costs and short-term stability.

What is needed, therefore, is a cell culture media which provides the essential nutritional, biological and biophysical requirements needed for cell growth at substantially less cost. For large-scale tank fermentation, an ideal culture media would provide superior performance in cell growth and maximum cell density, and still be easy to prepare from a relatively small number of low-cost ingredients. Preferably, the media should be serum-free. Also needed is a concentrated lipid emulsion which can supply critical lipids in a bioavailable form, but eliminates the need for lipid carriers such as serum, serum albumin, or other proteins from culture media.

SUMMARY OF THE INVENTION

The present invention solves the problems in the prior art through the provision of a low-cost, serum-free cell culture media, comprising a modified basal media having a novel formulation of free amino acids and vitamins, a peptone component which substitutes for the traditional serum component, and a lipid emulsion component.

DETAILED DESCRIPTION OF THE INVENTION

Figure 1:
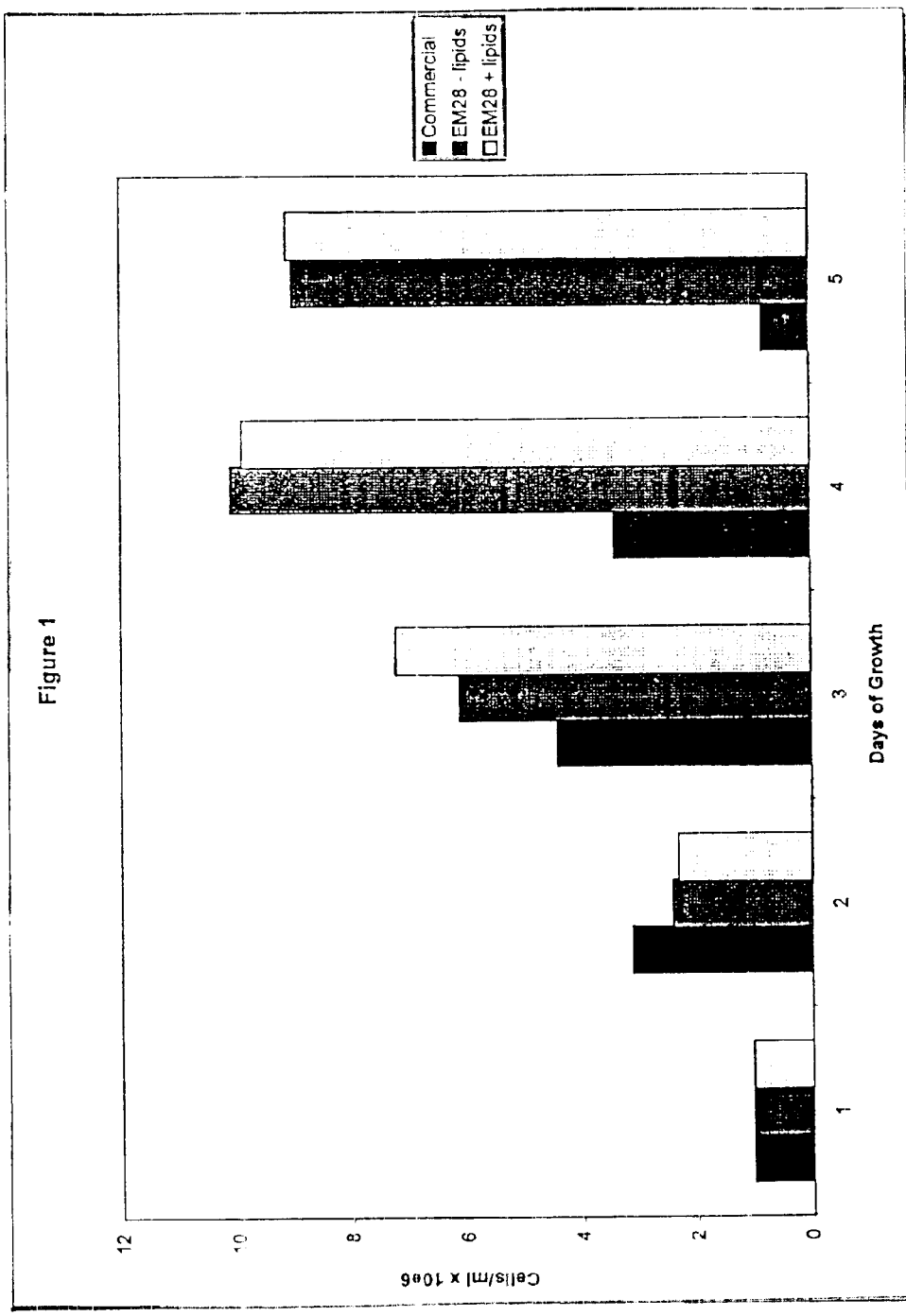
FIG. 1 is a graph illustrating the growth of *S. frugiperda* Sf-9 Cells in EM028 low-cost, serum-free media compared to growth in a typical commercially available serum free insect medium.

The starting point for most conventional cell culture media is a basic basal medium, typically comprising an established mixture of amino acids, minerals, sugars and inorganic salts in an aqueous solution, together with vitamins, organic acids and/or appropriate buffers. For most conventional media a suitable animal serum or serum albumin, together with a lipid component, is added to this basic basal medium to produce the complete media required to support cell life, growth, and reproduction, as well as for virus replication and the expression of recombinant or viral products.

Given the cost and the problems associated with the use of serum and/or serum albumin, several attempts have been made in the prior art to replace the serum component with another protein alternative. For example, U.S. Pat. No. 5,024,947, the disclosure of which is incorporated by reference herein, discloses a serum-free media consisting of 1) a conventional basal medium, 2) a lipid mixture, and 3) a peptone component, wherein the hydrolyzed protein products in the peptone component are intended to replace the proteins typically found in the serum or albumin. Although capable of supporting insect cell growth to densities equivalent to serum-containing media, the '947 patent includes expensive ingredients (such as hydroxyproline and organic acids) and does not support cell growth and virus infection cell densities at high enough levels to be economical for manufacturing. Thus, improvement is still needed, both in terms of the performance and the overall cost of the media.

Surprisingly, the present inventors have discovered that another expensive ingredient of the basic basal medium, the free amino acids, can also be substantially reduced or even eliminated when replaced with correspondingly larger amounts of less-expensive vitamins, sugars and peptones. This modification can be made without compromising the performance of the media. In fact, insect cells grown in the serum-free media of the present invention attain maximum cell densities twice that reported in the '947 patent and support productive virus infections at much higher cell densities. Thus, the complete serum-free media of the present invention provides additional cost savings in comparison with the serum-free compositions described in the prior art, while providing superior results.

The present invention also provides a novel method for producing the lipid component of cell culture media and the improved lipid emulsions produced thereby, for use in large scale preparations of cell culture media such as the serum-free media described above. Prior art techniques, such as that described in U.S. Pat. No. 5,372,943, the disclosure of which is incorporated by reference herein, require vigorous agitation such as sonication or vortexing to produce the emulsion. In contrast, the present invention employs a selective heating step which can spontaneously produce a concentrated lipid emulsion, thus eliminating the significant manufacturing costs associated with vigorous agitation of large volumes of liquid. Following the methods of the present invention, the emulsion forms spontaneously when the lipid component alone is heated, and a small volume of water at ambient temperature is added. Constant stirring can be advantageously employed to reduce the droplet size of the resulting emulsion.

Thus, the lipid emulsions of the present invention provide considerable cost savings and greatly simplify large-scale media production, since the sonication or vortexing of large volumes of liquid is not necessary. The improved emulsions obtained following the claimed method demonstrate superior stability in comparison with the emulsions produced in the prior art. As disclosed herein, the improved emulsions have a shelf life at least as long as six months and retain biological activity during this period. These lipid emulsions may be advantageously used in conjunction with the serum-free media of the present invention.

The preferred embodiment of the improved, serum-free media of the present invention comprises a modified basal medium, to which is added a peptone component, a lipid component and a protective component. The modified basal medium together with the additional components provide the basic nutrients necessary to support cell life, growth and reproduction.

I. Modified Low Cost Basal Media According to the Present Invention

The basal medium provides a nutrient mixture of inorganic salts, sugars, amino acids, vitamins, organic acids and/or buffers. The prior art teaches the use of commercially-available basal media based on established recipes [see, e.g., U.S. Pat. No. 5,024,947 at columns 7–8], which typically incorporate mixtures of free amino acids, free organic acids and vitamins. The phrases "free amino acid(s)", "free organic acids" and "free vitamin(s)" are used herein to refer to the purified preparations of individual amino acids, organic acids and vitamins which are commercially available from a number of companies, such as Sigma Chemical Company of St. Louis, Mo. These free amino acids, organic acids and vitamin preparations have either been purified from natural sources or are mass produced in a substantially purified form, and are conventionally added to the basic basal medium independent of any amino acids and/or vitamins derived from the peptone component of the complete medium. The free amino acids in particular represent a significant cost element of the basic basal media described in the prior art.

Unlike the prior art, the basal medium of the present invention has been modified so as to significantly reduce the amount of the costly free amino acids such as L-arginine HCl L-aspartic acid, L-asparagine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-valine in comparison with conventional media preparations. Surprisingly, the present inventors have discovered that one of the most expensive of the free organic acids, which include fumaric, malic, succinic and α-ketoglutamic acid and hydroxyproline, the amino acid hydroxyproline, can be eliminated entirely from the media with no ill effect. Since commercial preparations of this amino acid typically cost five to six times more than the next most expensive purified amino acid, the elimination of hydroxyproline imparts considerable costs savings for a large scale production, as does the overall reduction in free amino acids contemplated by the present invention.

In addition, in accordance with the present invention purified preparations of other individual organic acids, such as fumaric, malic, succinic and α-ketoglutamic, are significantly reduced, and can be eliminated from the formulation when the cell seeding density is increased by incorporating larger amounts of inexpensive vitamins like thiamin, riboflavin, niacin, vitamin B6, folic acid, vitamin B12, biotin, pantothenic acid, choline, para-aminobenzoic acid, Inositol, sugars like glucose and peptones like lactalbumin hydrolysate (e.g., Edamin S, available from Sigma Chemical Co., St. Louis, Mo., U.S.A.), yeast extracts such as Yeastolate (e.g., TC Yeastolate (Difco, U.S.A.), ox liver digests such as Panmede (Paines & Byrnes, Ltd., Great Britain), caseine digests such as Bactocasitone (Difco, U.S.A.), tryptose phosphate broth and any of a number of plant product hydrolysates (for example, the Hy Pep products from rice, wheat or soybean, Quest International). Thus, in a preferred embodiment, the serum-free media of the present invention comprises a basal medium having a reduced amount of free amino acids and other organic acids such as fumaric, malic, succinic and α-ketoglutamic acid, wherein the overall concentration of free amino acids in the basic basal medium before addition of the peptone component preferably ranges between approximately 0.1 and 6 g/l, more preferably between approximately 0.5 and 5 g/l, and most preferably between approximately 1 and 2 g/l in the basic basal medium. In comparison, a conventional basal medium such as Weiss et al's IPL-41 Medium (Weiss et al., *In Vitro* 17:495–502 (1981)) has a total free amino acid concentration of approximately 13 g/l.

In order to further improve cell growth, and to compensate for the reduction in free amino acids, the basal media of the present invention employs a significantly higher overall concentration of free vitamins than found in conventional prior art basal media. A major portion of the vitamins available in commercial serum free insect media is provided via the peptone component, typically by tissue culture grade (TC) Yeastolate (or other yeast extracts). TC yeastolate is a relatively expensive peptone, however, and can actually inhibit cell growth at high concentrations. The use of a higher concentration of free vitamins in the basic basal media of the present invention therefore represents a significant improvement over the prior art, particularly since it is cheaper to add small quantities of free vitamins than to add additional TC Yeastolate containing the same quantities of vitamins. This imparts a considerable cost savings when the media is produced in the large volumes required for tank fermentation. Thus, in the basal media according to the present invention the overall concentration of free vitamins in the basic basal medium before addition of the peptone component preferably ranges between approximately 0.02 and 0.1 g/l, more preferably between approximately 0.04 and 0.08 g/l, and most preferably between approximately 0.05 and 0.07 g/l. In comparison, the total concentration of free vitamins found in conventional formulations of basal media such as the IPL-41 medium of Weiss et al. is on the order of 0.02 g/l.

Thus, in the basal media of the present invention the ratio of free amino acids to free vitamins will range from about 1:0.01 to 1:0.1, usually from about 1:0.02 to 1:0.08, more usually from about 1:0.03 to 1:0.07, and most preferably from about 1:0.03 to 1:0.05. As demonstrated by the growth data provided in the experimental section below, however, this significant alteration to the basic composition of the basal media does not adversely affect the performance of the complete media.

Of course, the relative concentrations of each individual amino acid and vitamin can be adjusted according to the needs of the particular cell line. For example, although glutamine is essential for many insect cell lines, it is known in the art that some cell lines can grow without glutamine and may be able to synthesize it from precursors. See Mitsuhashi, *Appl. Entomol. Zool.* 22:533–36 (1987). Thus, depending on the intended use of the media one skilled in the art can easily adjust the concentrations of the individual free amino acids and vitamins to accommodate the known characteristics of the various insect cell lines.

II. The Peptone Component

The complete serum-free media of the present invention further comprises a peptone component, which also compensates for the reduction in free amino acids in the basic basal media, as well as providing a replacement for the serum or albumin. The term "peptone" is intended to refer to hydrolyzed protein products, typically a mixture of protein cleavage products produced by partial hydrolysis of a native protein using acid or enzyme and having average molecular weights between about 5 and 30 kD. Optionally, the individual peptone fractions combined to produce the peptone component will be prepurified by ultrafiltration or the like, to remove any residual proteases, endotoxins or other higher molecular weight products which could potentially interfere with the purification and use of recombinant products expressed by insect cells grown in the media.

The peptones contemplated for use in the present invention are therefore readily distinguishable from the higher molecular weight proteins supplied by serum, serum albumin and the like, which are eliminated from the media of the present invention. The total peptone concentration in the media will depend on a number of factors, such as the particular peptone fractions employed, the nature of the cell line to be cultured, the level at which a given peptone becomes toxic or inhibitory to cell growth, and the like, with the optimal concentration of each peptone fraction being determined empirically. Generally, the total amount of peptone in the complete serum-free media of the present invention will range from about 8 to about 30 g/l, more usually from about 12 to about 24 g/l.

Peptones suitable for use in the present invention are commercially available and include lactalbumin hydrolysate (e.g., Edamin S, available from Sigma Chemical Co., St. Louis, Mo., U.S.A.), yeast extracts such as Yeastolate (e.g., TC Yeastolate (Difco, U.S.A ), ox liver digests such as Panmede (Paines & Byrnes, Ltd., Great Britain), caseine digests such as Bactocasitone (Difco, U.S.A.), tryptose phosphate broth and any of a number of plant product hydrolysates (for example the Hy Pep products from rice, wheat or soybean, Quest International). A preferred embodiment of the peptone component comprises either TC Yeastolate, lactalbumin hydrolysate, or a combination of the two. In a particularly preferred and exemplary embodiment, the peptone component comprises a mixture of yeastolate and lactalbumin hydrolysate, each at a concentration of between about 6 and 14 g/l, more usually between about 7 and 13 g/l, and preferably between about 8 and 12 g/l.

III. Concentrated Lipid Emulsions and an Improved Method for Forming Same

The serum-free media of the present invention may further include a lipid emulsion component dissolved in an organic solvent. The prior art teaches the combination of these ingredients using a high energy input, vortexing method to emulsify the lipid solution in a 10% aqueous solution of Pluronic F-68 protectant. [See, e.g., '943 patent, col. 6, 11. 21–31]. Unfortunately, however, this method is difficult to perform and does not lend itself to scaling up for making large volumes of emulsion for use in manufacturing at the 1,000L to 10,000L level. The present invention solves these problems through the provision of a low-cost, readily-scalable formula and method for forming the lipid microemulsion. The emulsion thus formed is more stable and has a longer shelf life than prior art emulsions.

According to the present invention, the lipid emulsions of the present invention include the mixture of fatty acids, steroids, lipid-soluble vitamins and organic solvent as described in the prior art, with certain modifications. In the lipid emulsions of the present invention, the fatty acids comprise fatty acid esters, and more preferably, polyunsaturated fatty acid alkyl esters such as polyunsaturated fatty acid methyl esters. Fatty acid esters have a chain length of $C_{12}$ to $C_{22}$, preferred of $C_{13}$ to $C_{19}$. The alkylcomponent is $C_1$–$C_4$ alkyl (methyl, ethyl, n-proplyl, i-propyl, n-butyl, i-butyl, tert-butyl) wherein methyl is most preferred. A particularly preferred mixture of polyunsaturated fatty acid methyl esters is provided by fish liver oil, and more preferably, by cod liver oil, which also contains vitamin A. The formulation can also be simplified by using pure oleic acid fatty acid methyl ester instead of cod liver oil. The steroids are preferably sterols such as lanosterol, stigmasterol, sitosterol and cholesterol, and in a particularly preferred embodiment, cholesterol, while the lipid soluble vitamin is selected from the group consisting of phyllochinon (vitamin K1), menachinon (vitamin K2), menadion (vitamin K3), calciferol (vitamin D) cholecalciferol (vitamin D2), ergocalciferol (vitamin D3), retinol (vitamin A), alpha-tocopherol (vitamin E) and the non-acetylated form of alpha-tocopherol, wherein the non-acetylated form of alpha-tocopherol (vitamin E) is most preferred. Additionally, although a variety of alcohols $C_1$–$C_6$ alcohols are described for use in the prior art, the preferred organic solvent of the lipid emulsions of the present invention is n-propanol, i-propanol or a mixture of both, wherein n-propanol is most preferred.

A mixture of polyunsaturated fatty acid alkyl esters preferably methyl alkyl esters such as cod liver oil is preferably present at a final concentration in the complete media of from 1 mg/l to 50 mg/l; the steroid, preferably a sterol, most preferably cholesterol, is preferably at a concentration of 2 mg/l to 7 mg/l, the fat soluble vitamin, preferably non-acetylated alpha tocopherol is preferably at a concentration of 0.5 mg/l to 4 mg/l, and the alkhol, preferably n-propanol, is preferably at a concentration of 0.001% to 0.01%, more preferably of 0.002% to 0.005%, and most preferably of 0.0025% to 0.0035%. A final concentration of organic solvent which is non-toxic and non-inhibitory to cell growth is selected, depending on the chosen solvent, the type cells to be grown, and the like.

A surfactant is generally included in the lipid phase created by combining the above ingredients, prior to mixing with the aqueous phase and the consequent production of the lipid microemulsion. Preferably, the surfactant will be an anionic surfactant, usually a phospholipid or a non-ionic polymeric surfactant, usually a polysorbate, and preferably polysorbate 20 or polysorbate 80 (commercially available as Tween 80, ICI Americas Inc., Wilmington, Del., U.S.A.).

According to the method of the present invention, the above lipids are added to propanol and heated to a temperature of 40° C. to 70° C., and preferably of 50° C. to 60° C., with constant stirring until an anhydrous lipid phase is achieved. One or more small aliquots of water are then added to the lipid phase, again with constant stirring, and the mixture is cooled to room temperature. Although the emulsion generally forms spontaneously, stirring is usually required to reduce the droplet size such that it can be filter sterilized. The ratio of lipid to aqueous phases ranges from approximately 3:0.4 to 3:0.6 on a volume basis. A ratio of approximately 3:0.5 (v/v) is preferred. Additional organic solvent can be added as needed to maintain a liquid phase. A larger volume of water or 1% Pluronic F-68 can then be slowly added to the concentrated emulsion with constant stirring to facilitate long-term storage.

Importantly, and contrary to the teachings in the prior art (see '943 patent, cols. 6–8), the present inventors have determined that the presence of higher concentrations of protectants or other emulsifiers in the aqueous phase actually destabilizes the lipid microemulsion and greatly reduces the time the emulsion may be stored before addition to the basal medium. The method and formula of the present invention therefore solves a significant problem with prior art commercial lipid emulsions, which typically have a shelf life only days long and must be ordered or prepared immediately prior to use. In accordance with the preferred embodiment of the present invention, the concentration of emulsifier added to the aqueous component will be less than about 2%, more preferably less than about 1%, and most preferably no additional emulsifier will be added to the aqueous component of the lipid emulsion. The beneficial effects of these compounds in the overall media can be obtained by adding them separately to the complete medium, to avoid the stability problems they create in the emulsion component.

The microemulsion can be added directly to basal medium at this point and filter sterilized with the complete medium, or filter sterilized alone and stored refrigerated and in the dark for at least one month and usually up to six months. This method offers the advantages that it can be scaled up to any needed volume without special equipment, is easy to perform, and results in an emulsion with a long storage life, all characteristics needed to reduce media formulating costs for manufacturing purposes.

IV. Additional Components

Additional ingredients may also be added to the complete serum-free media of the present invention for a variety of purposes, such as, for example, a protective component to help prevent cell damage in agitated and/or sparged cell cultures. The protective component preferably comprises block copolymers of propylene oxide and ethylene oxide (polyoxypropylene polyoxyethylene condensates), and more preferably Pluronic polyols such as Pluronic F68 and F88 available from BASF Wyandotte Corp. (Parsippany, N.J., U.S.A.). Other suitable materials for use as protective components include hydroxyethyl starch, methyl cellulose, carboxymethyl cellulose, dextran sulfate, polyvinylpyrrolidone, ficoll, alginic acid, and polypropyleneglycol. As noted above, in accordance with the methods of the present invention the protective component is preferably added separately to the complete medium rather than combined with the lipid component as suggested in the prior art.

The media of this invention can also include other water-soluble ingredients, for example, insulin to enhance glucose uptake, transferrin for iron transport, trace elements as selenium, catalase as a peroxidation protectant, ethanolamine as a lipid precursor, steroid hormones such as testosterone, thyroid hormones such as triiodothyronine, nucleic acid precursors such as hypoxanthine, thymidine, deoxyadenosine, and deoxycytidine, as well as other nutrients contained in conventional serum-supplemented or serum free media for cell culture.

The method of preparing a culture medium is not critical. The medium may be prepared, for example, by dissolving all the ingredients and additives in water in their respective appropriate concentrations first and then filtering the solution on a membrane filter under pressure to get a sterilized culture medium. As noted above, when growing insect cells for the expression of recombinant or viral products, the peptone component of the media will preferably be prepurified, such as by prefiltration followed by ultrafiltration using a membrane having a molecular weight cutoff selected to be smaller than any recombinant or viral product that is to be collected to facilitate later purification.

The method of culturing cells with the medium of this invention is also not critical. Cells are cultured in the medium of this invention under approximately the same conditions as those for conventional culture media. In general, cells grown in the serum-free medium of this invention are cultured in a temperature range and under conditions appropriate for the particular cell line selected. For example, *Spodoptera frugiperda* cells, preferably Sf9 cells, are cultured in a temperature range of from about 20° C. to about 28° C. and wherein the pH of the culture medium is preferably maintained in a range from about 6 to about 7, more preferably about 6.2 to about 6.4. In some cases it may be advantageous to grow the cells under well-aerated conditions, that is, in agitated and/or sparged cultures. See, e.g., International Application No., PCT/US90/03756, published as International Publication No. WO 91/00341, the disclosure of which is hereby incorporated in its entirety.

In general, if insect, and especially Lepidopteran, cells can be grown successfully in media wherein serum, albumin, or other proteinaceous lipid carriers or other non-protein lipid carriers are employed, then the cells can be grown in the media of this invention wherein the serum or proteinaceous lipid carriers are replaced with peptones and a lipid microemulsion is provided, optionally together with other required hormones and growth factors. For example, there are a wide variety of commercially available media for insect cell culture which include such commercially-available basal media as, for example, TC10 without tryptose broth [commercially available from Microbiological Associates; see Gardiner et al., *J. Invert. Pathol,* 25:363 (1975)], Grace's Antheraea medium [Vaughn et al., *TCA Manual,* 3(1) (1976); Yunker et al., *Science,* 155:1565–1566 (1967)]. Medium M20 of Marks [Vaughn et al., *TCA Manual,* 3(1)(1976); Marks, In Kruse et al. (eds), *Tissue Culture Methods and Applications,* pp. 153–156 (1973)], Goodwin's IPL-52 Medium [Goodwin, *In Vitro,* 11:369–378 (1975)], Goodwin's IPL Medium [Goodwin et al., In Kurstak et al. (eds.), *Invertebrate Systems In Vitro* (1980)], Goodwin's IPL-76 Peptone Medium [Goodwin et al., id; Goodwin et al., *In vitro,* 14:485–494 (1978)], Hink's TNMFH Medium (Revised) [Hink, *Nature* (London), 226:466–467 (1970)], Medium S-301 of Hansen [Hansen, In Maramorosch (ed.), *Invertebrate Tissue Culture Research Applications,* pp. 75–99 (1976)]; Vaughn et al., *TCA Manual,* 3(1)(1976)], and the IPL-41 Medium discussed above [Weiss et al., *In Vitro,* 17(6):495–502 (1981)].

The media of this invention are employable not only for the growth of cells, but also for the production of useful physiologically active substances such as interferons, lymphokines and antibodies. Heterologous proteins that have been expressed in insect cells via a baculovirus expression vector system (BEVS) are outlined in Summers et al., *Banbury Report: Genetically Altered Viruses in the Environment,* 22:319–329 (1985). However, those skilled in the art who have the benefit of this disclosure, will recognize that many other recombinant proteins can be produced by animal, plant and/or microbial cells according to this invention. Exemplary recombinant proteins include, without limitation colony stimulating factors [for example, long and short form CSF-1 or M-CSF, 6-CSF, GM-CSF and interleukin-3 among others], modified pro-urokinase or urokinase, tissue plasminogen activator (TPA), TPA-urokinase hybrids, toxic proteins such as whole ricin toxin, ricin A chain, products containing ricin A, as well as, interferons α, β and γ and hybrids thereof), interleukins, tumor necrosis factor, erythropoletin and other hemotopoietic growth factors, human growth hormone, as well as porcine, bovine and other growth hormones, epidermal growth factor, insulin, hepatitis B vaccine, herpes simplex virus glycoprotein vaccines, superoxide dismutase, Factor VIII, Factor VIII C, atrial natriuretic factor, feline leukemia virus vaccines, as, for example, gp70 polypeptides, the light and heavy chains of antibody molecules, lectins such as *Ricin communis* agglutinin (RCA), diphtheria toxin, gelonin, exotoxin from *Pseudomonas aeruginosa,* toxic proteins from *Phytolacca americana* (PAPI, PAPII and PAP-s), insecticidal proteins from *Bacillus thuringiensis,* many enzymes as for example, CAT, as well as innumerable other hybrid proteins.

Although the exemplary embodiments described herein are adapted more specifically for use in insect cell culture, the present invention contemplates that media having the claimed characteristics can be advantageously used in the culture of virtually any cell type. The cells can be of animal, microbial or plant origin. If animal cells, they can be from vertebrates or invertebrates. Preferably, the cells are those which can produce recombinant, viral and/or natural products. Exemplary vertebrate cells are mammalian cells, for example, lymphocytes, fibroblasts, epithelial cells, ovarian cells, and their transformed cells, various neoplastic cells, and hybridomas derived therefrom. More specific examples of mammalian cells include Chinese Hamster Ovarian cells, Epstein-Barr Virus (EBV)-transformed human lymphoblastoid cell lines such as UMCL and C51804, human Burkitt's lymphoma-derived Namalwa cells, murine lymphoid cell-derived myeloma SPI cells, human fibroblast cells such as HEL and IMR-90, human tumor-derived epithelial cells such as HeLa-S$_3$ Hep-2 and KB, human primary cultured cells, rat Yoshida sarcoma cells, human fibroblast cells BHK-21, murine fibroblast cells 3T3, murine lymphoma cells YAC-1, human/mouse hybridomas such as stable cell line D-234-4-27-8 which produces anti-LPS IgM (ATCC No. HB 8598) and hybridomas which produce monoclonal antibodies to human fibroblast interferon as described in U.S. Ser. No. 325,969, filed Nov. 30, 1981.

Exemplary invertebrate cells are insect cells, preferably cells which can produce viral or recombinant products upon infection, respectively, with either wild-type viruses or recombinant baculoviruses and which have been shown to grow, reproduce and express recombinant and/or viral products in a medium containing serum, albumin, another protein and/or other lipid carriers. Such insect cell lines include *Bombyx mori, Lymantria dispar, Trichoplusia ni, Helicoverpa zea* and *Spodoptera frugiperda.* [See generally, Granados et al. (eds.), *The Biology of Baculoviruses* (CRC Press 1986); Vaughn, Adv. *Cell, Cult.,* Maramorosch (ed.), *Invert. Tissue Culture; Research Applics.,* p. 295 (1976); and Vaughn, In, Barigozzi (eds.) *Proceedings of Internatl. Collq. Invert. Tissue Culture,* (2nd, Tremezzo, 1967), p. 119 (1968).]

Further, insect cells that can be grown in the media of the present invention are preferably from any order of the Class Insecta which can be hosts to a baculovirus expression vector system, or other wild-type viruses, but are preferably from the Diptera or Lepidoptera orders. About 300 insect species have been reported to have nuclear polyhedrosis virus (NPV) diseases, the majority (243) of which were isolated from Lepidoptera. [Weiss et al., Cell Culture Methods for Large-Scale Propagation of Baculoviruses, In Granados et al. (eds.), *The Biology of Baculoviruses*: Vol. II Practical Application for Insect Control, pp. 63–87 at p. 64 (1986).] Insect cell lines derived from the following insects are exemplary: *Carpocapsa pomonella* preferably cell line CP-128); *Trichoplusia ni* (preferably cell line TN-368); *Autographa californica; Spodoptera frugiperda* (preferably cell line Sf9); *Lymantria dispar; Mamestra brassicae; Aedes albopictus; Orgyia pseudotsugata; Neodiprion sertifer; Aedes aegypti; Antheraea eucalypti; Gnorimoschema opercullela; Galleria mellonella; Spodoptera littoralis; Drosophila melanogaster, Heliothis zea; Spodoptera exigua; Rachiplusia ou; Plodia interpunctella; Amsacta moorei; Agrotis c-nitrum, Adoxophyes orana, Agrotis segetum, Bombyx mori, Hyponomeuta malinellus, Colias eurytheme, Anticarsia gemmetalis, Apanteles melanoscelus, Arctia caja,* and *Lymantria dispar.* Preferred insect cells are from *Spodoptera frugiperda,* and especially preferred is cell line Sf9 (ATCC CRL 1711). Other *S. frugiperda* cell lines, such as IPL-Sf21AE III, are described in Vaughn et al., *In Vitro,* 13:213–217 (1977).

The preferred insect cell lines cultured in the media of this invention are suitable for the reproduction of numerous insect-pathogenic viruses such as picornaviruses, parvoviruses, entomopox viruses, baculoviruses and rhabdoviruses, of which nucleopolyhedrosis viruses (NPV) and granulosis viruses (GV) from the group of baculoviruses are preferred. Further preferred are NPV viruses such as those from Autographa spp., Spodoptera spp., Trichoplusia spp., Rachiplusia spp., Galleria spp. and Lymantria spp. More preferred are baculoviruses strains *Autographa californica* NPV (AcNPV), *Rachiplusia ou* NPV, *Galleria mellonella* NPV and any plaque-purified strains of AcNPV, such as E2, R9, S1, M3, characterized and described by Smith et al., *J. Virol.,* 30:828–838 (1979); Smith et al., *J. Virol.,* 33:311–319 (1980); and Smith et al., *Virol.,* 89:517–527 (1978).

Experimental

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); g (grams); mg (milligrams); kg (kilograms); $\mu$g (micrograms); L (liters); ml (milliliters); $\mu$l (microliters); cm (centimeters); mm (millimeters); $\mu$m (micrometers); nm (nanometers); EC (degrees Centigrade); h (hours); min (minutes); sec (seconds); msec (milliseconds).

The individual materials described below were purchased from Sigma Chemcial Company, St. Louis Mo., with the exception of TC Yeastolate, DF5577-08, which was obtained from VWR Scientific, Brisbane, Calif.

EXAMPLE 1

Preparation of Serum Free Media

A specific embodiment of the serum-free media of the present invention, labeled EM028, was prepared using the ingredients and amounts listed in Table 1:

TABLE 1

| COMPONENT | Concentration (g(ml)/l) |
|---|---|
| CaCl$_2$ | 0.5 g |
| 50X Major Salts | 20 ml |
| 500X Minor Salts | 2 ml |
| Difco yeastolate | 8 g |
| Edamin S | 10 g |
| 50X Vitamins | 20 ml |
| glucose | 7.5 g |
| glutamine | 2 g |
| 33X amino acids | 30 ml |
| Lipid Emulsion | 11 ml |
| 10% Pluronic F-68 | 10 ml |
| NaHCO$_3$ | 0.7 g |

(X = fold dilution)

The lipid emulsion was prepared as described in Example 2 below. The liquid concentrates were prepared with the components and amounts listed in Tables 2 through 4 below. The concentrates and powdered components were added in the order listed in Table 1 above to 800 ml of water. The pH of the final mixture was then adjusted to 6.3 and the volume brought up to 1 liter.

TABLE 2

50X VITAMINS

| COMPONENT | CONCENTRATION (mg/l) |
|---|---|
| Thiamin | 32.64 |
| Riboflavin | 89.6 |
| Niacin | 576 |
| Vitamin B6 | 92 |
| Folic acid | 11.88 |
| Vitamin B12 | 15 |
| Biotin | 11.896 |
| Pantothenic acid | 361.6 |
| Choline | 1908 |
| para-Aminobenzoic acid | 16 |
| Inositol | 20 |

TABLE 3

50X MAJOR SALTS

| COMPONENT | CONCENTRATION (50X g/l) |
|---|---|
| KCl | 65.65 |
| MgSO$_4$ (anhydrous) | 46.17 |
| NaCl | 150.31 |
| NaH$_2$PO$_4$ · H$_2$O | 58.00 |

TABLE 4

500X MINOR SALTS

| COMPONENT | CONCENTRATION (500X mg/l) |
|---|---|
| CoCl$_2$ · 6H$_2$O | 76.68 |
| CuCl$_2$ · 2H$_2$O | 108.58 |
| MnCl$_2$ · 4H$_2$O | 38.82 |
| FeSO$_4$ · 7H$_2$O | 1469.85 |
| ZnCl$_2$ | 603.64 |
| (NH$_4$)$_6$Mo$_7$O$_{24}$ · 4H$_2$O | 20.00 |

The amino acids, with the exception of glutamine, were prepared according to Table 5 below:

TABLE 5

33X AMINO ACIDS

| COMPONENT | CONCENTRATION (500X g/l) |
|---|---|
| L-arginine HCl | 4.00 |
| L-aspartic acid | 6.50 |
| L-asparagine | 7.39 |
| L-cystine 2HCl | 0.65 |
| L-glutamic acid | 7.50 |
| L-glycine | 1.00 |
| L-histidine F.B. | 1.00 |
| L-isoleucine | 3.75 |
| L-leucine | 1.25 |
| L-lysine HCl | 3.50 |
| L-methionine | 5.00 |
| L-phenylalanine | 5.00 |
| L-proline | 2.50 |
| L-serine | 2.00 |
| L-threonine | 1.00 |
| L-tryptophan | 0.50 |
| L-valine | 2.50 |
| L-tyrosine 2Na-2H$_2$O | 1.82 |

The above amino acids, with the exception of tyrosine, are added to 900 ml of water in the order given above in Table 5. If an individual amino acid fails to dissolve in a reasonable amount of time, 6N HCl can be added until the pH is 1.7. After all of the other amino acids have been added, the tyrosine is dissolved in 50 ml of water and added slowly to the previous mixture. The final volume is then adjusted to 1 liter.

EXAMPLE 2

Preparation of Lipid Emulsion

TABLE 6

| COMPONENT | QUANTITY (g/L) |
|---|---|
| Cod Liver Oil Fatty Acid Methyl Esters | 1.0 |
| Cholesterol | 0.45 |
| Alpha-Tocopherol | 0.2 |
| Tween 80 | 2.5 |

The surfactant and lipid ingredients were added to a large glass beaker and heated gently to about 50° C. to 60° C. The mixture was stirred continuously with a magnetic stir bar until the solids melted and a liquid phase was achieved. While continuing to heat and mix, 0.5 ml of water was slowly added, followed by 1.3 ml propanol. The mixture was cooled to room temperature, then another 1.7 ml of propanol was added with mixing to again achieve a liquid phase. Then, 8.3 ml of water or 1% Pluronic F-68 in water was added dropwise with mixing. The stirring rate was increased and 0.8 ml of water or 1% Pluronic was added. The mixture was heated gently for 15 minutes with stirring (the temperature was kept below 40° C.) and water or 1% Pluronic was added to bring the volume up to 1.0L. In order to store the emulsion for later use, the emulsion was filter sterilized and refrigerated.

EXAMPLE 3

Long Term Stability of Lipid Emulsion

Table 7 demonstrates the long term stability of the lipid emulsion produced using the procedure described in this patent. The maximum cell density achieved and AcMNPV PIB production of Sf9 cells grown in three different lots of EM28 medium are presented. Lots 10 and 11 were made with 7 month old lipid emulsions containing cod liver oil fatty acid methyl esters or pure oleic acid fatty acid methyl ester, respectively. All other solutions were freshly prepared. Lot 12 was made using freshly prepared solutions and lipid emulsion (the lipid emulsion contained the cod liver oil fatty acid methyl esters). For virus production, cultures were infected at a density of $1.8 \times 10^6$ cells/ml.

TABLE 7

| EM28 LOT | MAX CELL DENSITY (cells/ml) | VIRUS PRODUCTION (PIBs/ml) |
|---|---|---|
| Lot 10 | $10.5 \times 10^6$ | $1.2 \times 10^8$ |
| Lot 11 | $10.3 \times 10^6$ | $1.0 \times 10^8$ |
| Lot 12 | $10.3 \times 10^6$ | $1.0 \times 10^8$ |

EXAMPLE 4

Production of PIBs

Table 8 illustrates the production of AcMNPV baculovirus polyhedral occlusion bodies (PIBs) by Sf9 cells growing in either a commercially-available serum-free insect medium (Excell 401, JRH Biosiences, Lanexa, Kans.) or EM028 medium with and without the lipid microemulsion. The cells were infected at a density of $2.4 \times 10^6$ cells/ml in shake flasks.

TABLE 8

| MEDIUM USED | VIRUS PRODUCTION (PIBs/ml) |
|---|---|
| Commercial serum free | $4.0 \times 10^7$ |
| EM028 without lipid emulsion | $5.0 \times 10^6$ |
| EM028 with lipid emulsion | $1.5 \times 10^8$ |

It is evident from the above results that cells grown in the low-cost, serum-free medium of the present invention can achieve cell densities superior to those described for prior art serum-free media formulations (FIG. 1). The present invention medium also supports productive replication of Baculoviruses in high density cell cultures at lower cost. Furthermore, Example 3 demonstrates the superior stability of the lipid emulsion produced according to the present invention.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. For example, the relative amounts of the individual components set forth in Tables 1–6 can be modified by one of skill in the art in accordance with the specific needs of the particular cell line of interest, which needs are well known and readily available to one of skill in the art. Generally, the specific amounts recited in Tables 1–6 above can vary by up to approximately 50%, and more preferably, by up to approximately 20%.

We claim:

1. A method for producing a lipid emulsion at large scale for use in cell culture media, said method comprising:
    combining in an organic solvent a surfactant and a mixture of lipids to create a lipid phase, wherein said lipids are selected from the group consisting of fatty acids, sterols, and lipid-soluble vitamins;
    heating said lipid phase to a temperature of 40° C. to 70° C. to create an anhydrous lipid phase; and
    adding an aqueous phase to said anhydrous lipid phase to produce a stable lipid micro-emulsion, wherein said aqueous phase consists of water.

2. A method according to claim 1, wherein said temperature is of 50° C. to 60° C.

3. A method according to claim 1, wherein said organic solvent is n-propanol, I-propanol or a mixture of both.

4. A method according to claim 1, wherein said lipid soluble vitamin is non-acetylated alphatocopherol.

5. The lipid emulsion produced according to the method of claim 1.

* * * * *